(12) United States Patent
Barski et al.

(10) Patent No.: US 7,853,063 B2
(45) Date of Patent: Dec. 14, 2010

(54) METHOD FOR PRODUCING A CROPPED MEDICAL IMAGE

(75) Inventors: Lori L. Barski, Mendon, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 1083 days.

(21) Appl. No.: 11/499,584

(22) Filed: Aug. 4, 2006

(65) Prior Publication Data

US 2008/0031505 A1 Feb. 7, 2008

(51) Int. Cl.
*G06K 9/00* (2006.01)
(52) U.S. Cl. .................. 382/132; 382/128; 382/131
(58) Field of Classification Search ............ None
See application file for complete search history.

(56) References Cited

U.S. PATENT DOCUMENTS

| | | | |
|---|---|---|---|
| 4,620,098 A | 10/1986 | Fujiwara | |
| 6,047,204 A | 4/2000 | Ogawa | |
| 6,081,267 A | 6/2000 | Stockham et al. | |
| 6,091,841 A | 7/2000 | Rogers et al. | |
| 6,317,510 B1 | 11/2001 | Murakami | |
| 6,587,596 B1 | 7/2003 | Haeberli | |
| 6,654,506 B1 * | 11/2003 | Luo et al. | 382/282 |
| 6,704,440 B1 | 3/2004 | Kump | |
| 7,606,406 B2 * | 10/2009 | Matsuno | 382/132 |
| 2002/0122534 A1 | 9/2002 | Polkus et al. | |
| 2004/0258292 A1 | 12/2004 | Matsuno | |

FOREIGN PATENT DOCUMENTS

| | | |
|---|---|---|
| EP | 0 599 097 A2 | 6/1994 |
| WO | WO 2005/008598 | 1/2005 |

OTHER PUBLICATIONS

Rafael Wiemker et al., "Automated recognition of the collimation field in digital radiography images by maximization of the Laplace area integral," Proceedings of the SPIE—The International Society for Optical Engineering SPIE-Int. Soc. Opt. Eng USA, vol. 3979, 2000, pp. 1555-1565, XP002506904.

* cited by examiner

*Primary Examiner*—Tom Y Lu
*Assistant Examiner*—Thomas A Conway

(57) ABSTRACT

A method of displaying a digital medical image. The steps include acquiring a digital medical image; determining from the acquired digital medical image the anatomically relevant region which defines the relevant image boundaries; and determining an optimum virtual plate size from a stored plurality of virtual plate sizes for displaying the anatomically relevant regions of the digital medical image on a display device. In one arrangement, the acquired digital medical image has associated exam information (such as bodypart and image projection), the plurality of virtual plate sizes are stored by exam information, and the optimum plate size is determined, at least in part, by the exam information associated with the digital medical image.

16 Claims, 10 Drawing Sheets

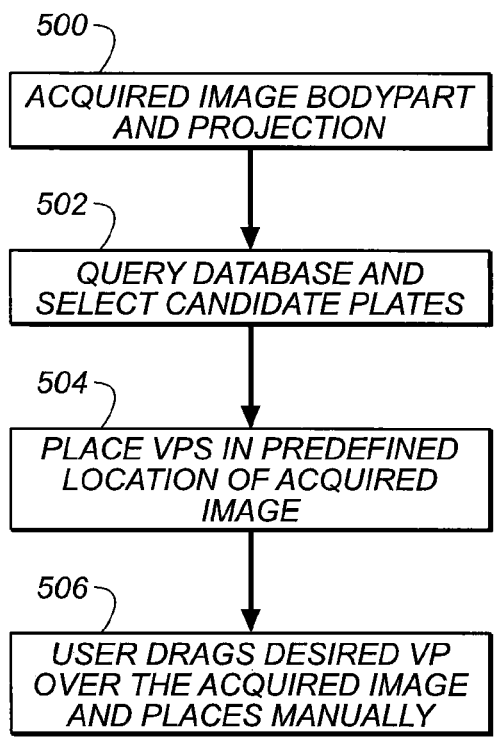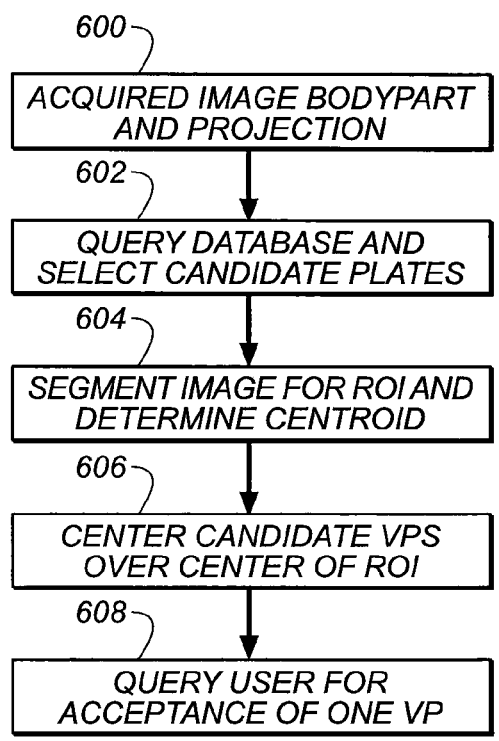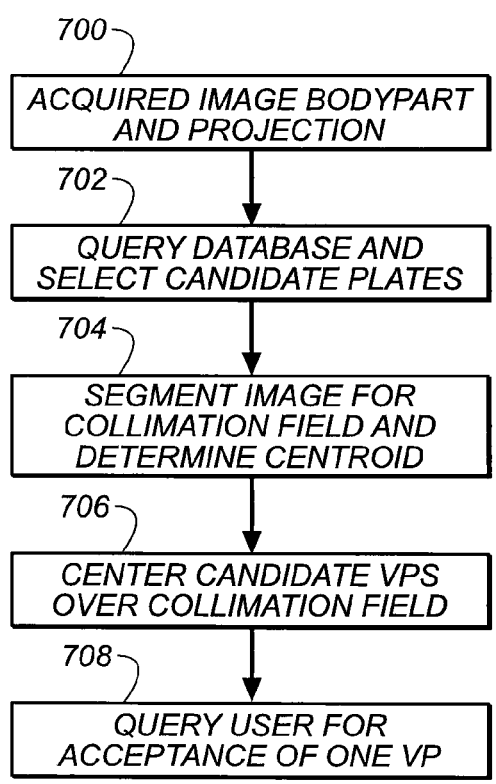

METHOD FOR PRODUCING A CROPPED MEDICAL IMAGE

FIELD OF THE INVENTION

This invention relates in general to digital medical imaging and more particularly to the processing and displaying on a display of digital medical images acquired by computed radiography (CR) and direct radiography (DR) systems.

BACKGROUND OF THE INVENTION

Analog film/screen projection radiography supports conventional film sizes (e.g., 18×24 cm., 24×30 cm., 35×35 cm., and 35×43 cm.) that are selected based upon the size of the object (bodypart) being imaged. Digital systems such as computed radiography (CR) and direct radiography (DR), are replacing analog film radiography systems for various reasons—for example, improved image quality and network distribution of information. CR utilizes storage phosphor cassettes, which are a direct replacement of analog film cassettes, thus, cassette sizes are the same and selection of the plate is dictated by the bodypart being examined. If a small anatomical structure is being imaged, e.g., a finger, the smallest (e.g., 18×24 cm.) plate is typically used. When the CR image is read out and sent to a workstation for interpretation, it will be properly displayed on a high resolution display without appreciable further manipulation by the end-user (radiologist, diagnostician). This is typically because the sizes of the cassettes and the resolution of the image capture are consistent with the image area and pixel resolution available on the display.

A common practice in CR that is carried over from analog film practices is using a larger cassette to capture multiple views of a bodypart on a single cassette. When this is done, typically the image containing multiple views is displayed to fill the full screen (referred to as "fit-to-screen") causing the anatomy to be smaller than true size. The end-user is forced to pan and zoom the image prior to interpretation which is inefficient and undesirable.

Direct (and indirect) radiography (DR) is an alternate newer technology for obtaining digital projection radiographs. DR utilizes a flat-panel imager which incorporates a thin film transistor (TFT) array to convert incident x-rays to discrete pixels via photodiodes (indirect conversion) or storage capacitors (direct conversion). The DR flat-panels are large area fixed size devices, typically 35×43 cm. or 43×43 cm. with the resulting image having a corresponding large image area. Thus, as mentioned above, a small anatomical structure acquired on a large area DR panel typically results in wasted time by the end-user in panning and zooming the image when the image is displayed on a workstation in a "fit-to-screen" mode.

Display of projection radiographs is typically managed by a picture archiving and communication system (PACS) and industry standards exist which facilitate interoperability between vendors. The standards are defined by the Digital Imaging and Communications in Medicine (DICOM) organization and subcommittees. DICOM has made provisions for display protocols to facilitate appropriate soft-copy presentation of an image for diagnostic interpretation. For example, DR modalities which utilize the direct x-ray information object definition (DX IOD) can specify "field of view" information as part of the DX detector module attributes. Utilization of this aspect of DICOM can facilitate good management of images for display in PACS. But some aspects of the standards are optional, and not all PACS vendors implement the optional features. Thus, in some situations, dependent upon the acquisition modality (e.g., CR or DR IOD tags) and PACS vendor's DICOM implementation and capabilities, inefficient of the radiologist's time may be required. Therefore, it becomes the responsibility of the modality (CR or DR) to most efficiently manage the information being sent to the PACS—either by supplying information about the exposure field in the form of DICOM information, or by cropping extraneous information to efficiently utilize bandwidth, both from the perspective of digital data transmission, and data storage in the archive.

There is a need for an imaging process which solves this problem, namely, that large area projection radiographic images (DR or larger cassette CR) are more efficiently handled (displayed, transmitted, and stored) when exams of smaller anatomical structures are acquired.

U.S. Pat. No. 6,654,506, issued Nov. 25, 2003, inventors Luo et al., discloses a method for automatically creating cropped and zoomed versions of photographic images. The method uses a probalistic approach to automatically determine a crop window. A belief map is required a prior in which a belief value at a particular pixel location indicates an importance of a photographic subject at the same location in the photographic image. The belief map drives the placement of the crop window, the size of which is set by the user in advance as an input to the system. The user specifies the crop size (i.e., the crop window) and a magnification factor as input to the processing. This process, although useful for the purpose for which it was intended, may be disadvantageous in using subject probability and in requiring these latter inputs.

U.S. Pat. No. 6,091,841, issued Jul. 18, 2000, inventors Rogers et al., discloses a method and system for segmenting desired regions in digital mammograms. The method is related to automatic microcalcification detection and classification and discloses an automated segmentation method which utilizes iterative morphological operations in combination with signal normalization (via histogram equalization) and region growing to define a binary mask of a breast image. The crop window is then defined as the rectangular boundary that encompasses the binary mask. There is no provision for a rotated exposure field crop window such that a rotated crop window would result, nor is there provision for multiple exposure fields.

U.S. Pat. No. 4,620,098, issued Oct. 28, 1986, inventor Fujiwara, is directed to a radiation photographing apparatus.

U.S. Pat. No. 6,081,267, issued Jun. 27, 2000, inventors Stockham et al. relates to a method for displaying radiological data.

U.S. Pat. No. 6,317,510, issued Nov. 13, 2001, inventor Murakami is directed to a blackening processing method and apparatus.

U.S. Pat. No. 6,704,440, issued Mar. 9, 2004, inventor Kump is directed to a method and apparatus for processing a medical image.

SUMMARY OF THE INVENTION

According to the present invention, there is provided a solution to the problems and a fulfillment of the needs discussed above.

In one embodiment of the present invention, all similar exams, independent of the acquisition modality, are consistent in size and centering upon display. In the case of DR acquisition of a smaller bodypart, the image is analyzed to define an appropriate image format or "virtual plate that would have been used had the medical image been captured on a smaller cassette (CR or analog screen/film) system. In the case of a large cassette CR acquisition, the image is analyzed to define all of the relevant exposure fields (one or multiple may exist) and define an appropriate "virtual plate" for each.

According to a feature of the present invention, there is provided a method of displaying a digital medical image comprising: acquiring a digital medical image; determining from said acquired medical image the anatomically relevant region which defines the relevant image boundaries; and determining an optimum virtual plate size from a stored plurality of virtual plate sizes for displaying said anatomically relevant region of said digital medical image on a display device.

The present invention has some advantages. For example, there is a lower bandwidth for the transmission and storage of data. There is a more consistent presentation of CR and DR medical images when both modalities are used at a PACS system. There is improved workflow for end-users (radiologists) who don't have to spend time magnifying and panning images. Also, CR customers can lessen their dependency on smaller plate sizes and use larger plates to acquire all images, and then apply the "virtual plate" to make the image consistent in size to what is expected based upon analog film practices.

BRIEF DESCRIPTION OF THE DRAWINGS

FIGS. 8-10 are block diagrams of methods of selecting the VP based on known bodypart and projection information of an acquired image.

DETAILED DESCRIPTION OF THE INVENTION

Referring now to the figures, there will be described the present invention in greater detail. In one aspect of the present invention, a method is provided which solves the problem experienced by radiologists when viewing a DR medical image. The radiologist may waste valuable time panning and zooming the DR image before being able to make an interpretation (diagnosis) because the full field of DR data is sent from the image capture modality, though the usable image may only occupy a portion of the sent image. According to the invention, an analysis is performed on the DR image to define the appropriate "Virtual Plate" which would have been used had the medical image been captured via CR or analog film. The "Virtual Plate" is a usually rectangular outline having the physical dimensions of an imaging plate used in CR and analog film radiography which is an overlay on the medical image presented on a high resolution display.

Figure 1:
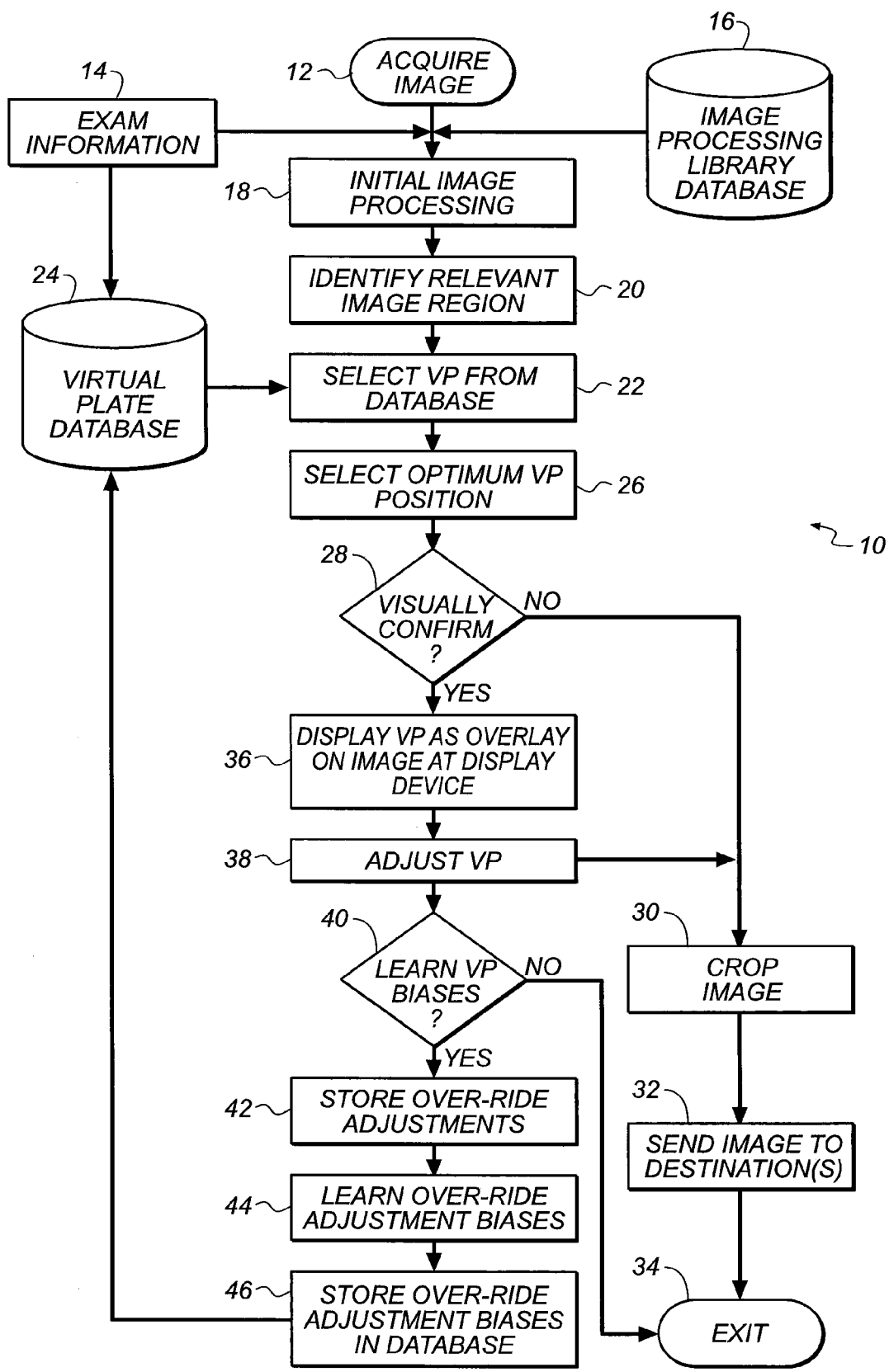
FIG. 1 is a block diagram of an overview of the present invention.

FIG. 1 is a block diagram of an overview of the present invention. The method 10 includes acquiring a digital medical (radiographic) image (item 12), from a DR or CR image capture device. Using exam information 14 (such as bodypart and image projection) associated with the acquired image, and using image processing algorithms from image processing library database 16, the acquired image is initially processed (item 18). The digital image is then processed to identify the relevant image region (item 20). Appropriate virtual plates (VP) are selected (item 22) from a Virtual Plate Database (item 24. Note, when visual confirmation of the VP is being performed, multiple virtual plates are possible to allow maximum flexibility by the user. The optimum VP position relative to the relevant image region is then selected (item 26). An optimum VP position is defined as the placement and possible rotation of the VP, which results in the least amount of relevant image data being excluded (cropped out). If it is decided (item 28) not to visually confirm the selected VP, the image is then cropped (item 30). Cropping involves removing unnecessary information from the image. The cropped image with VP overlay is then sent to the appropriate destination (s) (item 32) (such as a radiologist's high resolution display for interpretation), and the method is exited (item 34).

If it is decided to visually confirm the selection of the VPs (item 28), the VPs are displayed as an overlay on the image at a display device (item 36). The best VP (size) position (and possibly rotation) can be adjusted (item 38). The processed image is then cropped using the adjusted VP according to items 30, 32, and 34. If it is decided (item 40), not to learn the VP adjustment biases generated at item 38, the method is exited (item 34). If it is decided to learn the VP biases (item 40), the over-ride adjustments are stored (item 42), the over-ride adjustment biases are learned (item 44), and the over-ride adjustment biases are stored (item 46) in the Virtual Plate Database 24.

More specific aspects of the method shown in FIG. 1 will now be described. The identification of a relevant image region of an acquired medical image (item 20 of FIG. 1) can be effected as follows using known segmentation techniques specific to digital projection radiograph images: (1) identifying the direct exposure regions of the acquired medical image, if they exist; (2) identifying the collimator regions of the acquired medical image, if they exist; (3) identifying the anatomical region of interest in the acquired medical image; and (4) combining the information from (1)-(3) to define the anatomically relevant region of the acquired medical image which defines the relevant image region boundaries. The principle axis orientation of the anatomically relevant region is determined if the user chooses to allow VP rotation. A prior user input is required for VP rotation due to slight geometric distortions which might occur and which is a well-known consequence of image rotation.

After identifying the relevant image region boundaries and principle axis orientation, a VP is selected (item 22 of FIG. 1). If visual confirmation of the VP is desired, then: (1) if the "relevant image boundaries" fits within a candidate VP 9a plurality of VPs are possible), the user selects that VP and it becomes the size of the "desired plate size". An overlay of the VP is placed onto the original for confirmation at a display device; (2) if the "relevant image boundaries" do not fit within the VPs, a plate size is selected, which minimizes the amount of relevant image data to be cropped. This defines which VP is used and it is overlaid onto the acquired image for confirmation at a display device. (This allows the user to not only see the placement of the VP, but also enables the user to translate and rotate the VP manually); and (3) upon confirmation, the corresponding acquired image information which is under the VP is cropped (and potentially rotated) and a new output image is formed. Note that the user may choose to not use any of the VP candidates and thus do no cropping of the image data.

If visual confirmation is not desired and the method is carried out in a fully automatic mode, then: (1) if the "relevant image boundaries" are too large for the "desired plate size", the plate size is selected which minimizes the ROI data which would be cropped; (2) the VP is oriented correctly; (3) the VP is centered; and (4) the corresponding acquired image information which is under the VP is cropped (and potentially rotated) to form a new image.

Figure 2:
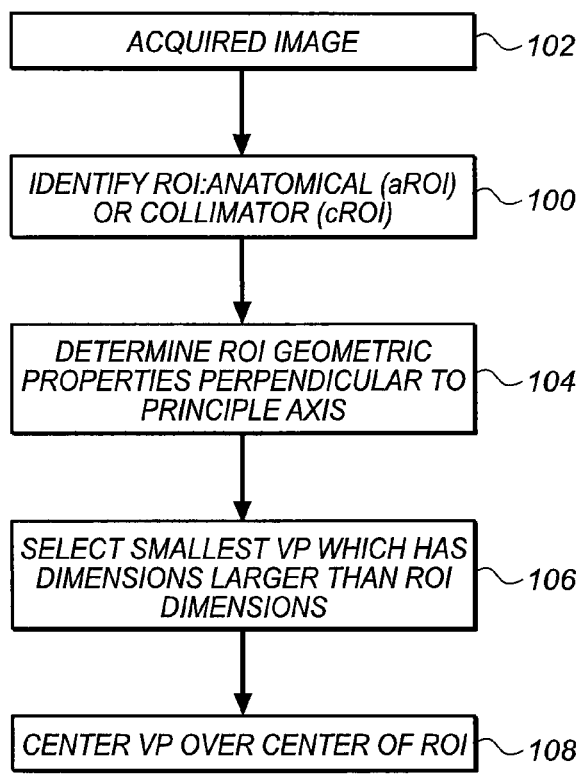
FIG. 2 is a block diagram of a method of selecting a VP according to the present invention.
Figure 3:
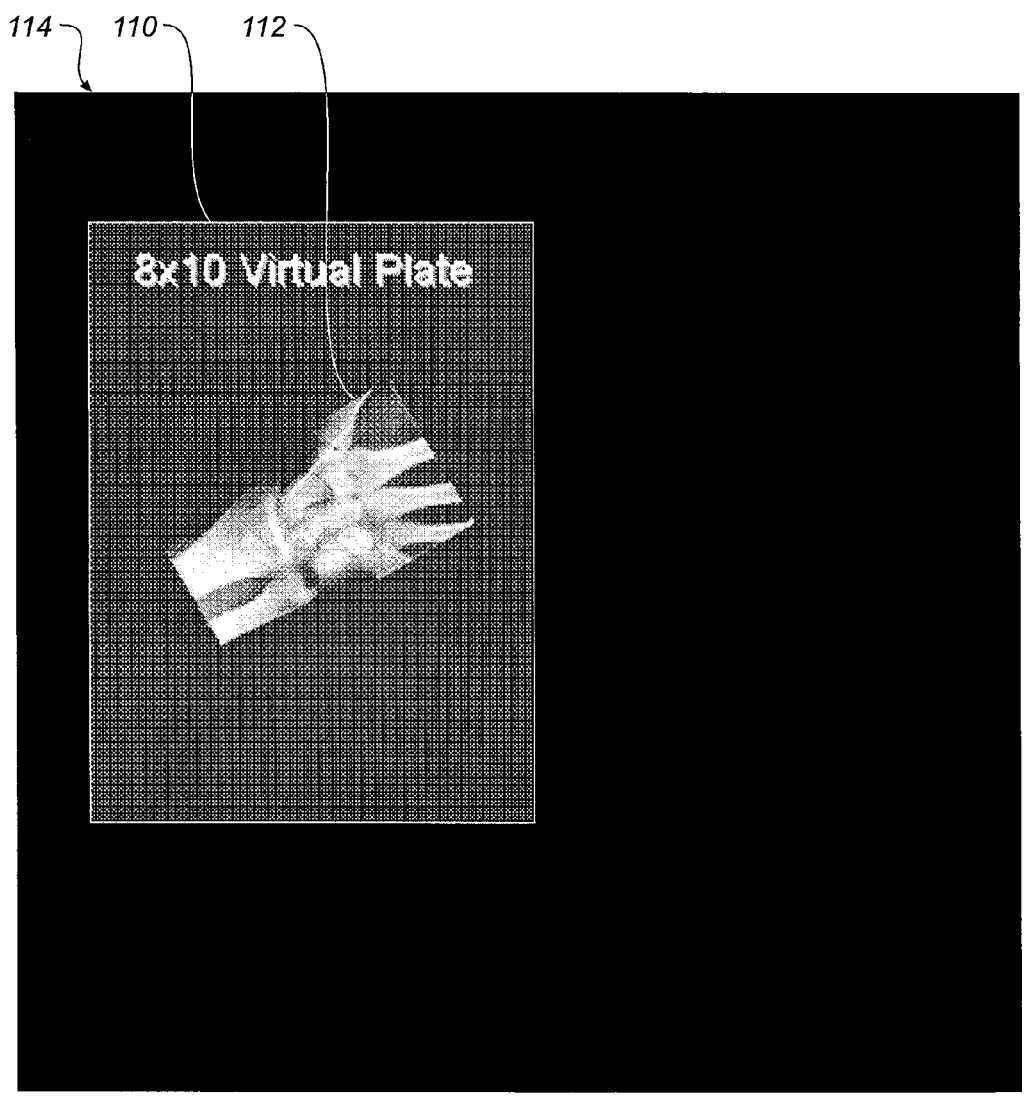
FIG. 3 is a diagrammatic view illustrating the method of FIG. 2.

Following are several methods of selecting the VP. As shown in FIGS. 2 and 3, one method is to analyze the acquired medical image to define the radiation field and to select the smallest VP which will encompass the radiation field (without rotation). The method includes: identifying the Region Of Interest (ROI), either anatomical (aROI) or collimator (cROI) (FIG. 2—item 100) from the acquired image (item 102); determining ROI geometric properties (size, perimeter, center, and centroid) (item 104); selecting the smallest VP which has dimensions larger than the ROI dimensions (item 106); and centering the ROI over the center of the VP (item 108), to create a new output image. This is shown in FIG. 3, where 8×10 Virtual Plate 110 is shown as an overlay on ROI 112, all within image 114. (Note: VP sizes are given in inches). This method can be carried out automatically.

Figure 4:
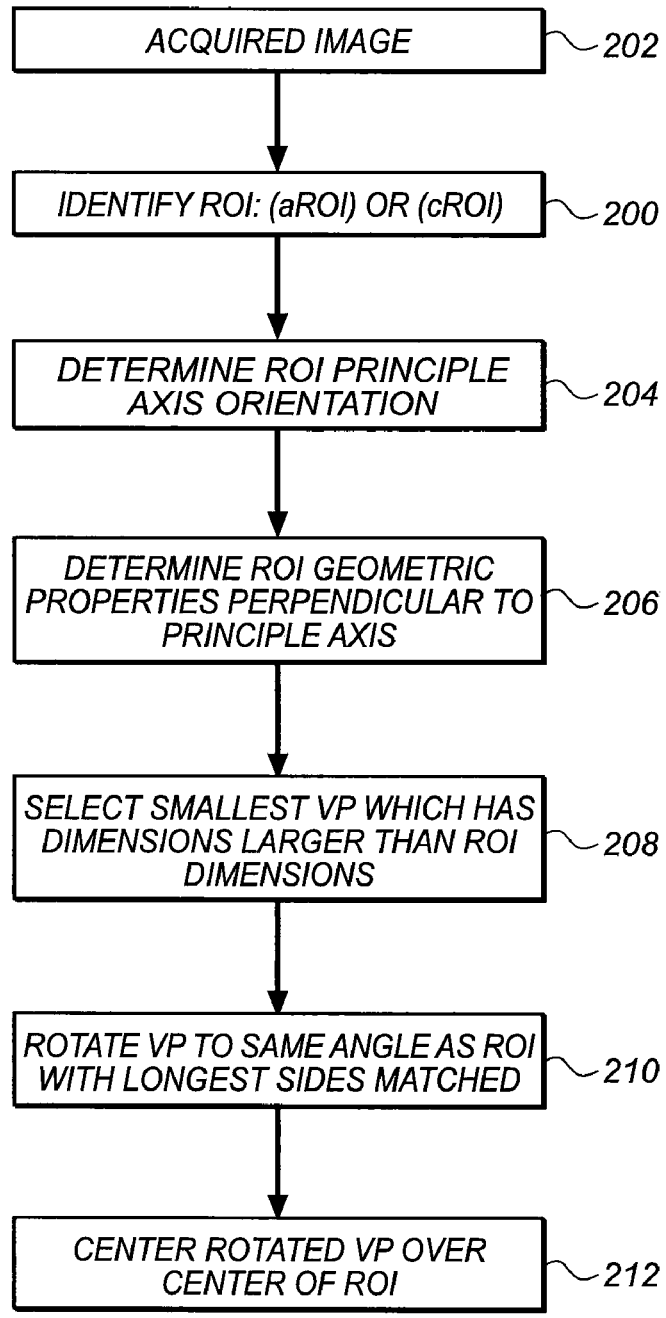
FIG. 4 is a block diagram of another method of selecting a VP according to the present invention.
Figure 5:
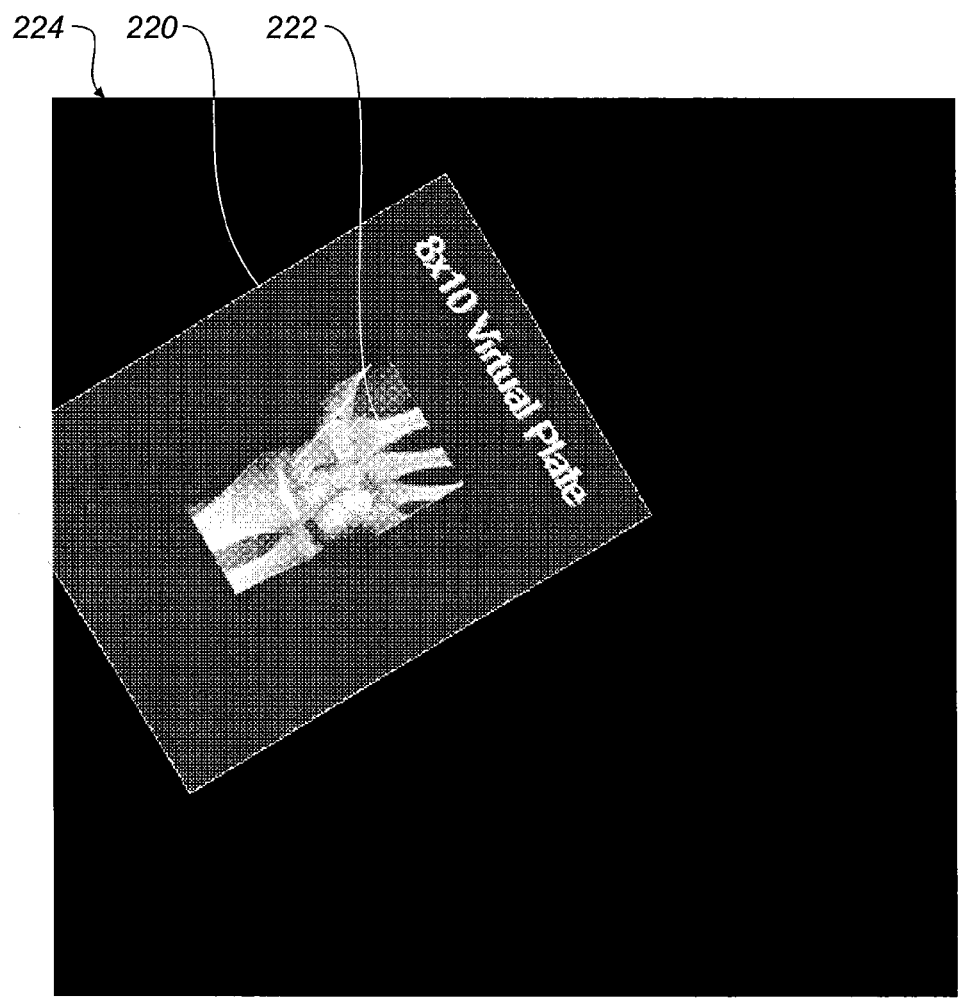
FIG. 5 is a diagrammatic view illustrating the method of FIG. 4.

FIGS. 4 and 5 illustrate the latter method with rotation. The modified method includes: identifying the ROI (aROI or cROI) (FIG. 4—item 200) of the acquired image (item 202); determining ROI principal axis orientation (item 204); determining ROI geometric properties along the principle axis (item 206); selecting the smallest VP which has width and height dimensions larger than ROI dimensions in the principle axis orientation (item 208); rotating VP to same angle as ROI with longest sides matched (item 210); and centering the ROI over the center of the rotated VP (item 212). This is shown in FIG. 5, where 8×10 Virtual Plate 220 is shown as an overlay on ROI 222, all within image 224. The VP has been automatically rotated along the same principle axis as the image.

Figure 6:
FIG. 6 is a diagrammatic view illustrating another method according to the present invention.

FIG. 6 illustrates an application where automatic VP processing is not preferred and requires user acceptance. In this application, the 8×10 VP 300 and the 10×12 VP 302 cut through the anatomical structure 304 in acquired image 306.

Figure 7:
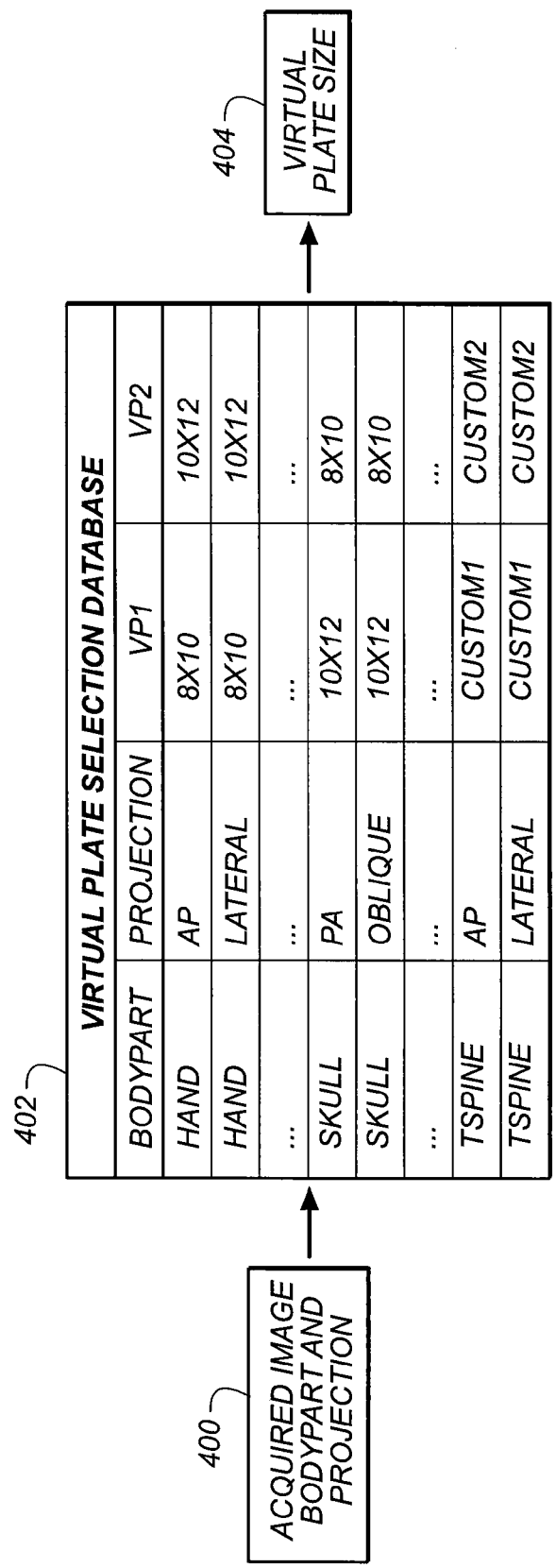
FIG. 7 is a graphical view of a portion of a Virtual Plate selection database useful in carrying out the methods of FIGS. 8-10.

Following are methods of selecting a VP based on parameters of the acquired image, viz. bodypart and image projection. FIG. 7 illustrates a portion of a VP selection database that can be stored in VP database 24 in FIG. 1. As shown, the columns are respectively labeled "Bodypart", "Projection", "VP1" and "VP2". (Note: "AP" projection is Anterior-Posterior projection and "PA" projection is Posterior-Anterior projection). As an example, if the acquired image 400 has bodypart and projection parameters associated with it of "skull" and "PA", the Virtual Plate Size 404 selection VP1 in database 402 is a 10×12 VP and VP2 is an 8×10 VP. The methods shown in FIGS. 8-10 can use the VP selection database of FIG. 7 as an example.

The method shown in FIG. 8 involves indexing a database of VP configurations by bodypart and projection and includes: providing the bodypart and projection information of an acquired image (item 500), querying the VP database 24 and selecting the candidate VP plate(s) (item 502), placing the VPs in a predefined location of the acquired image (item 504), and having the user dragging the desired VP over the acquired image and placing it manually (item 506).

The method shown in FIG. 9 involves indexing a database of VP configurations by bodypart and projection and positioning the VP based upon ROI analysis and includes: providing the bodypart and projection information of an acquired image (item 600); querying the VP database and selecting candidate VP plates (item 602); segmenting the image for ROI and determining the centroid (item 604); centering the candidate VPs over the center of the ROI (item 606); and querying the user for acceptance of one VP (item 608).

The method shown in FIG. 10 involves indexing a database of VP configurations by body part and projection and positioning a VP based on collimated region and includes: providing the bodypart and projection of an acquired image (item 700); querying the VP database and selecting candidate VP plates (item 702); segmenting the acquired image for collimation field and determining the centroid of the collimation field (item 704); centering the candidate VP over the collimation field (item 706); and querying the user for acceptance of one of the VPs (item 708). If the bodypart and projection are not known, simply index BP=UNKNOWN, Projection=UNKNOWN and VP1 and VP2 are defined by the user.

Figure 11:
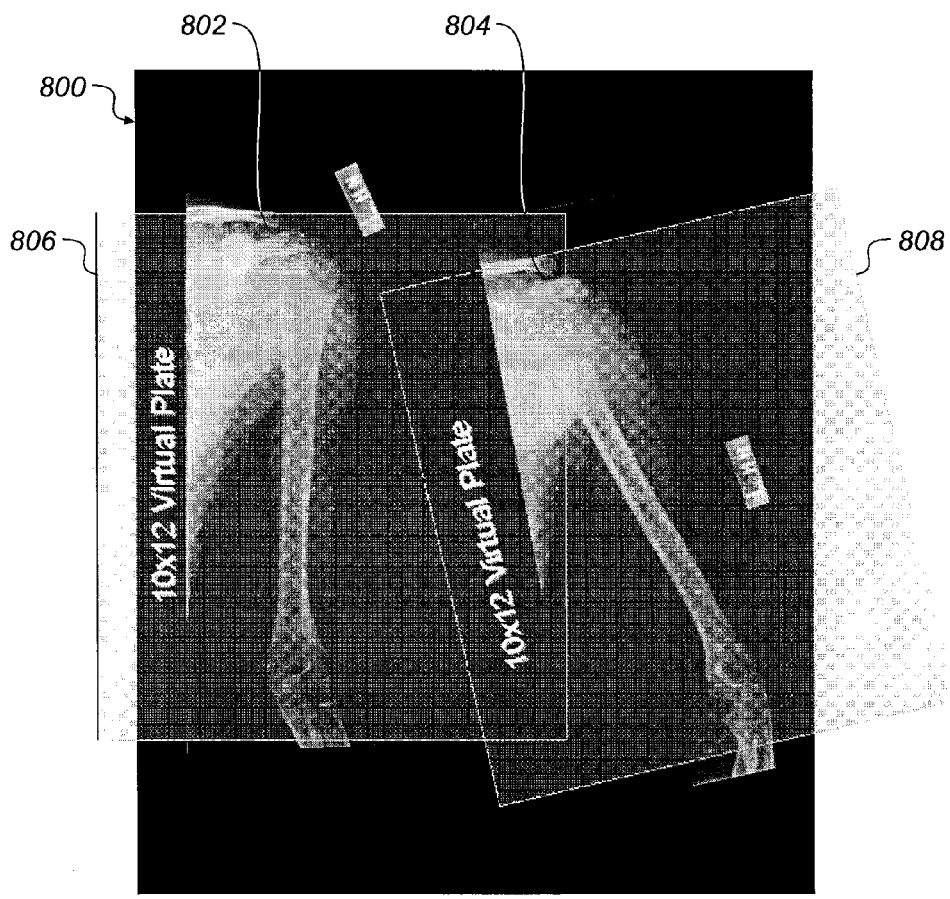
FIG. 11 is a diagrammatic view illustrating a method according to the present invention where the acquired medical image has multiple exposures.

Another aspect of the present invention pertains to CR systems where multiple exposures are made on a single CR plate, as customers migrate from analog film practices to new digital capabilities; the practice of making multiple exposures on a single plate lingers, mostly from the desire to reduce film costs when primary interpretation is done on laser film. As these customers move to reading on PACS display systems, the desire to have single images in the archive increases. The virtual plate processing techniques of the invention can be utilized to assist in cropping these images to improve consistent presentation at the PACS display device. This method involving multiple exposure acquisition requires user acceptance of placement of the VPs. As shown in FIG. 11, acquired medical image 800 has multiple exposure images 802 and 804. The method of the invention has produced 10×12 Virtual Plates 806 and 808 overlaid, respectively on images 802 and 804. The images 802 and 804 can then be cropped and can be stored as individual files in a PACS system.

The method of the invention can be expanded to define "desired VP plate sizes" to be non-traditional sizes which are appropriate for smaller exams such as extremities. These custom VP plates are illustrated as the last two entries in the database shown in FIG. 7.

Figure 12:
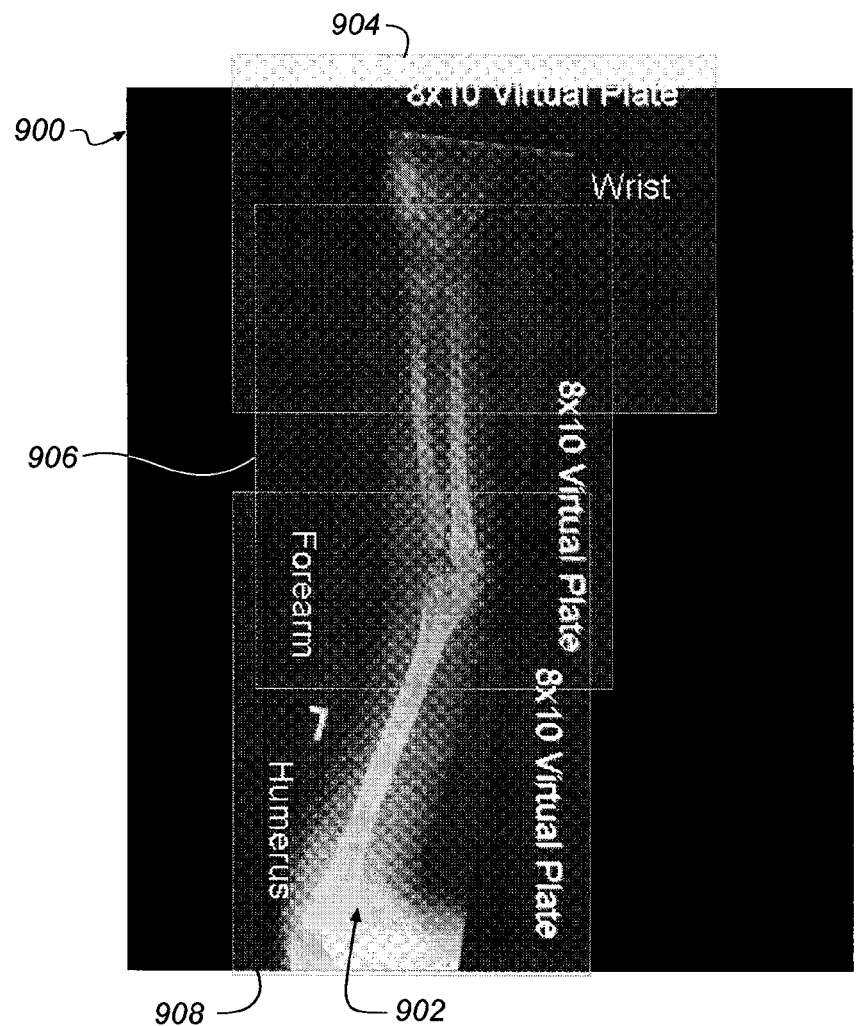
FIG. 12 is a diagrammatic view illustrating a method according to the present invention where multiple exams are extracted from one acquired medical image.

Still another aspect of the present invention pertains to multiple exams from one medical image acquisition. As shown in FIG. 12, acquired medical image 900 includes an elongated anatomical image 902. Image 902 can be presented as multiple images according to the invention by producing VPs overlaid on segments of image 902. Thus, as shown, 8×10 VPs 904, 906, and 908 are overlaid respectively on the wrist, forearm, and humerus of the image 902. These images can then be cropped and can be stored as individual files in a PACS system.

The invention has been described in detail with particular reference to certain preferred embodiments thereof, but it will be understood that variations and modifications can be effected within the spirit and scope of the invention.

PARTS LIST

10—method
12—acquiring
14—exam information

16—image processing library database
18—initially processed
20—relevant image region
22—VP selected
24—Virtual Plate database
26—optimum VP position selected
28—visual confirmation not decided
30—image cropped
32—sending
34—exiting
36—VP displayed
38—VP size adjusted
40—VP biases not learned
42—Store over-ride adjustments
44—learn over-ride adjustments
46—biases stored
100—identifying ROI
102—acquired image
104—determining
106—selecting
108—center VP
110—VP
112—ROI
114—image
200—identifying
202—acquired image
204—determining
206—determining
208—selecting
210—rotating
212—center VP
220—VP
222—ROI
224—image
300, 302—VP
304—anatomical structure
306—acquired image
400—acquired image exam data
402—database
404—Virtual Plate size
500—acquired image exam data
502—query
504—place VPs
506—user drags desired VP
600—acquired image bodypart and projection
602—Query
604—segment
606—center candidate VPs
608—Query user
700—acquired image bodypart and projection
702—query database
704—segment image
706—center candidate
708—query user
800—acquired medical image
802, 804—multiple exposure images
806, 808—VPs
900—acquired medical image
902—anatomical image
904, 906, 908—VPs

The invention claimed is:

1. A method of displaying a digital medical image, the method comprising the steps of:
acquiring a digital medical image;
determining from said acquired medical image the anatomically relevant region which defines the relevant image boundaries; and
determining a virtual plate size from a stored plurality of virtual plate sizes for displaying said anatomically relevant region of said digital medical image on a display device; wherein said virtual plate size has the conventional physical dimensions of an imaging plate used in computed radiography and analog film radiography.

2. The method of claim 1 wherein said acquired digital medical image has exam information associated with it, wherein said stored plurality of virtual plate sizes are stored by exam information, and wherein said virtual plate size is determined, at least in part, by said exam information associated with said digital medical image.

3. The method of claim 2 wherein said exam information includes bodypart and image projection information.

4. The method of claim 1 including the step of cropping said image for display with said virtual plate size.

5. The method of claim 1 including the step of employing a virtual plate having said determined virtual plate size, rotating said virtual plate to properly align it with said acquired digital medical image for displaying said anatomically relevant region of said digital medical image on a display device.

6. The method of claim 1 including the step of carrying out initial image processing on said acquired digital medical image before determining said anatomically relevant region.

7. The method of claim 1 wherein said method is carried out without visual confirmation of the virtual plate size by a user.

8. The method of claim 1 wherein said method is carried out with visual confirmation of the virtual plate size by a user.

9. The method of claim 1 wherein said method requires visual confirmation by a user because the virtual plate size cuts through the anatomically relevant region.

10. The method of claim 1 including the step of storing virtual plate information into DICOM fields for transmission and display of processed image data.

11. The method of claim 1 wherein said determining from said acquired image step includes: identifying the anatomically relevant region of interest (ROI) of said acquired digital medical image; and determining a ROI size in order to determine the anatomically relevant region which defines the relevant image boundaries; wherein said stored plurality of virtual plate sizes includes different virtual plate sizes; and wherein said determining the virtual plate size step includes selecting a smallest virtual plate size which has a size larger than the ROI size.

12. The method of claim 1 wherein said determining from said acquired image step includes: identifying the anatomically relevant region of interest (ROI) of said acquired digital medical image; wherein said ROI has a principal axis orientation; determining the ROI principal axis orientation; and determining a ROI size along and perpendicular to the determined principal axis in order to determine the anatomically relevant region which defines the relevant image boundaries; wherein said stored plurality of virtual plate sizes includes different virtual plate sizes; and wherein said determining the virtual plate size step includes selecting a smallest virtual plate size which has a size larger than the ROI size.

13. The method of claim 1 wherein said acquiring step includes acquiring a digital medical image having associated exam information, including bodypart and image projection; wherein said determining from said acquired image step includes segmenting the acquired digital medical image having associated exam information for region of interest (ROI), which said ROI has a center and determining its center; and wherein said determining the virtual plate size step includes querying a database of virtual plate selections and selecting candidate virtual plates from the database as a function of associated exam information; and centering the candidate virtual plates over the center of the ROI; and including a step of querying a user of said method for acceptance of one of the candidate virtual plates centered over the center of the ROI.

14. The method of claim 1 wherein said acquiring step includes acquiring a digital medical image having associated exam information, including bodypart and image projection; wherein said determining from said acquired image step includes segmenting the acquired digital medical image having associated exam information for collimation field and which collimation field has a center and determining its center; and wherein said determining the virtual plate size step includes querying a database of virtual plate selections and selecting candidate virtual plates from the database as a function of associated exam information; and centering the selected candidate virtual plates over the collimation field; and including a step of querying a user of the method for acceptance of one of the candidate virtual plates centered over the collimation field.

15. The method of claim 1 wherein said acquiring step includes acquiring a digital medical image having multiple exposures, wherein each of said multiple exposures has an anatomically relevant region; wherein said determining from said acquired medical image step includes determining from said acquired digital medical image the anatomically relevant regions of said multiple exposures which define the relevant image boundaries of each said determined anatomically relevant region; and wherein said determining the virtual plate size step includes determining for each anatomically relevant region one virtual plate size from said stored plurality of virtual plate sizes for displaying said anatomically relevant region on a display device.

16. The method of claim 1 wherein said determining from said acquired medical image step includes determining from said acquired medical image a plurality of anatomically relevant regions which defines the relevant image boundaries for each such anatomically relevant region; and wherein said determining the virtual plate size step includes determining one virtual plate size from said stored plurality of virtual plate sizes for each anatomically relevant region of said plurality of anatomically relevant regions for displaying each of said anatomically relevant region of said digital medical image on said display device.

* * * * *